(12) United States Patent
Zanon

(10) Patent No.: US 7,338,249 B1
(45) Date of Patent: Mar. 4, 2008

(54) SAMPLE PLATE GRIPPING MECHANISM

(75) Inventor: Stephen Zanon, Campbell, CA (US)

(73) Assignee: Thermo Finnigan LLC, San Jose, CA (US)

( * ) Notice: Subject to any disclaimer, the term of this patent is extended or adjusted under 35 U.S.C. 154(b) by 400 days.

(21) Appl. No.: 11/171,674

(22) Filed: Jun. 30, 2005

(51) Int. Cl.
*B25J 15/00* (2006.01)
*H01J 49/00* (2006.01)

(52) U.S. Cl. .................. 414/741; 250/288

(58) Field of Classification Search .......... 414/741, 414/969, 730, 936; 250/288
See application file for complete search history.

(56) References Cited

U.S. PATENT DOCUMENTS

| | | | |
|---|---|---|---|
| 6,592,324 B2 * | 7/2003 | Downs et al. .......... 414/741 |
| 6,670,609 B2 * | 12/2003 | Franzen et al. ........ 250/288 |
| 2003/0057368 A1 * | 3/2003 | Franzen et al. ........ 250/281 |
| 2003/0108450 A1 * | 6/2003 | Mainquist et al. ...... 422/99 |
| 2004/0141887 A1 * | 7/2004 | Mainquist et al. ...... 422/102 |
| 2006/0188940 A1 * | 8/2006 | Cima et al. ............ 435/7.1 |

\* cited by examiner

*Primary Examiner*—Robert Kim
*Assistant Examiner*—Johnnie L Smith, II
(74) *Attorney, Agent, or Firm*—Sharon Upham

(57) ABSTRACT

An apparatus for releasably gripping a sample plate for use with a mass spectrometer has been developed, the sample plate having substantially parallel faces and a peripheral surface. The apparatus comprises a planar member and first and second guiding structures. The second guiding structure comprises a biasing mechanism which when activiated, provides a force that forces the second guiding structure towards the peripheral surface of the sample plate such that the sample plate is retained by the apparatus. Utilization of the configuration reduces frictional point contact thus reduces localized stress point resulting in yielding the surface material thus in effect guarding both sample plate and first guiding means from galling and/or reducing any type of material removal when gripping a sample plate, or releasing a sample plate.

20 Claims, 5 Drawing Sheets

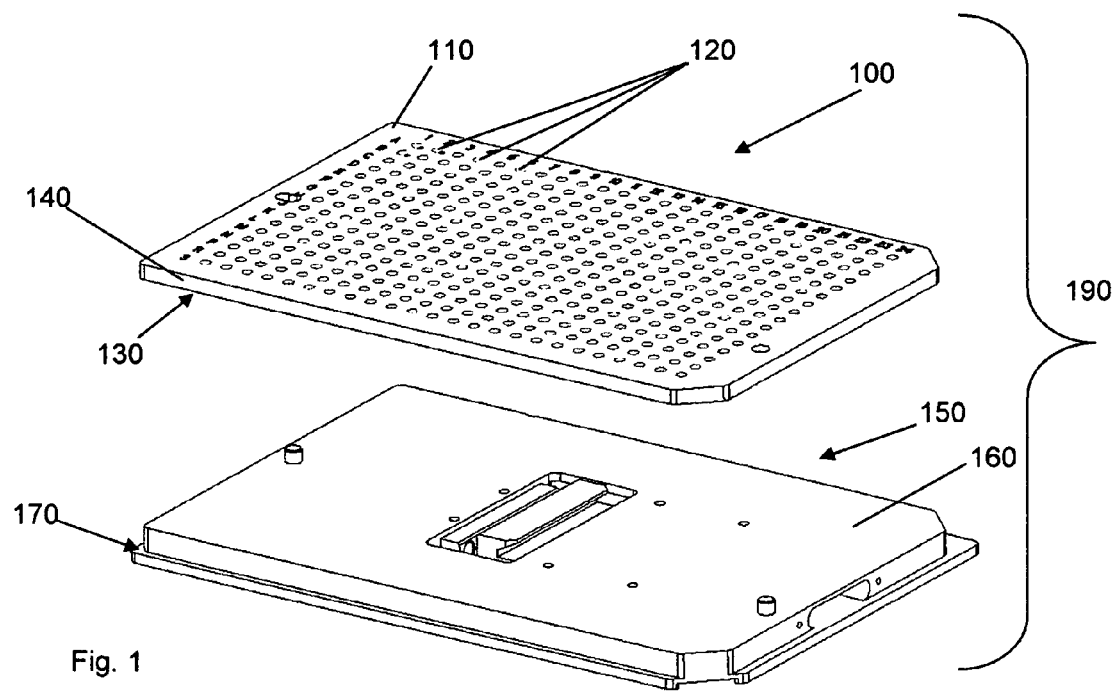
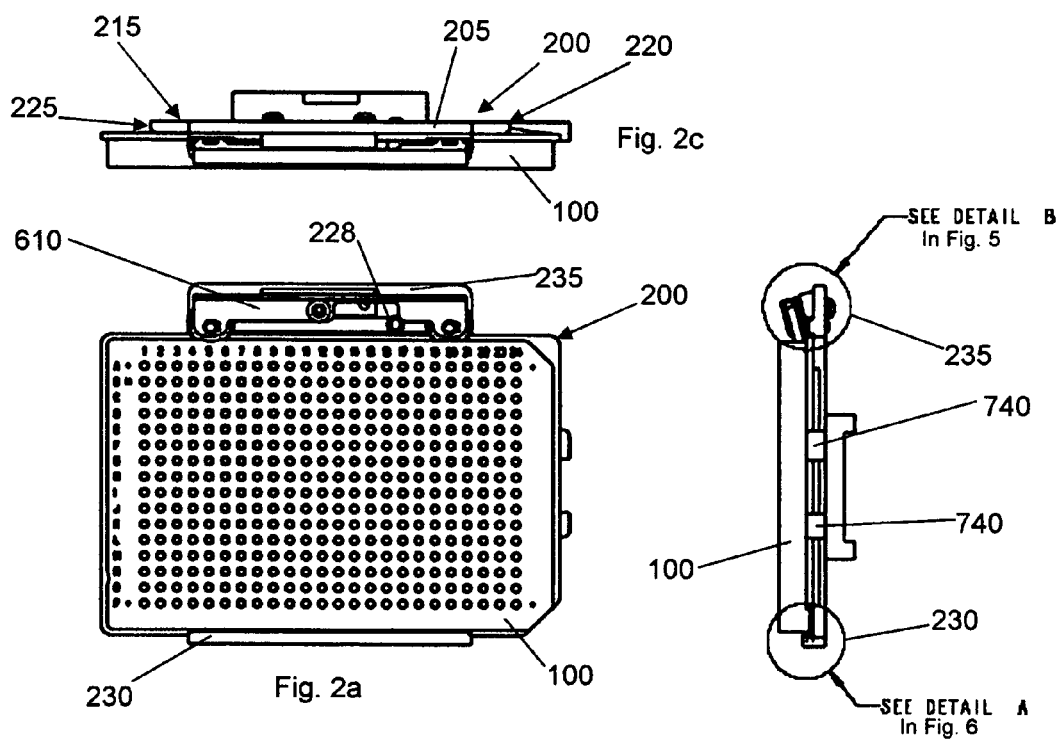

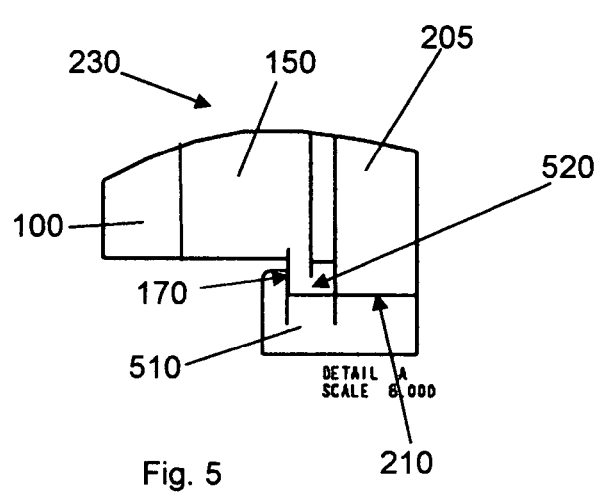
Fig. 5
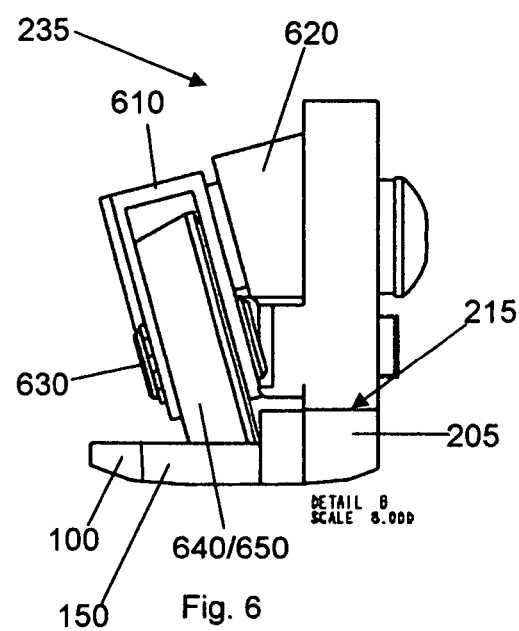
Fig. 6
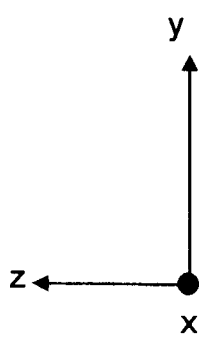

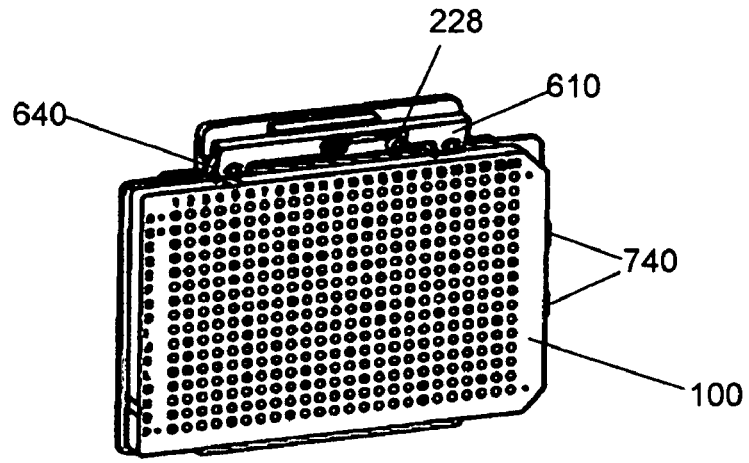
Fig. 7c
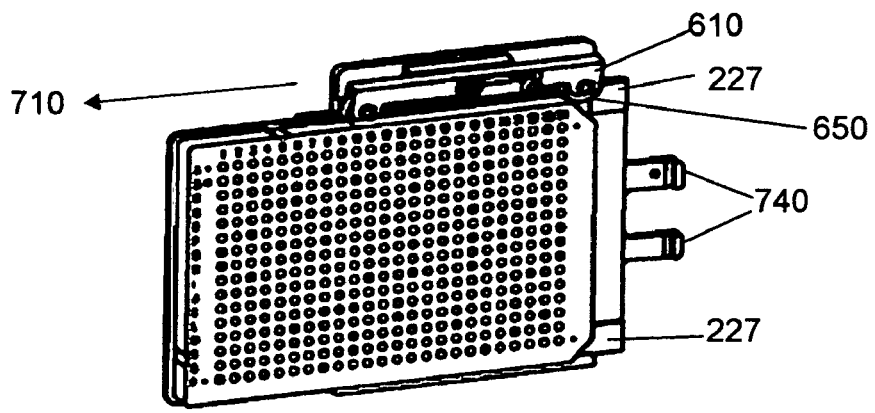
Fig. 7b
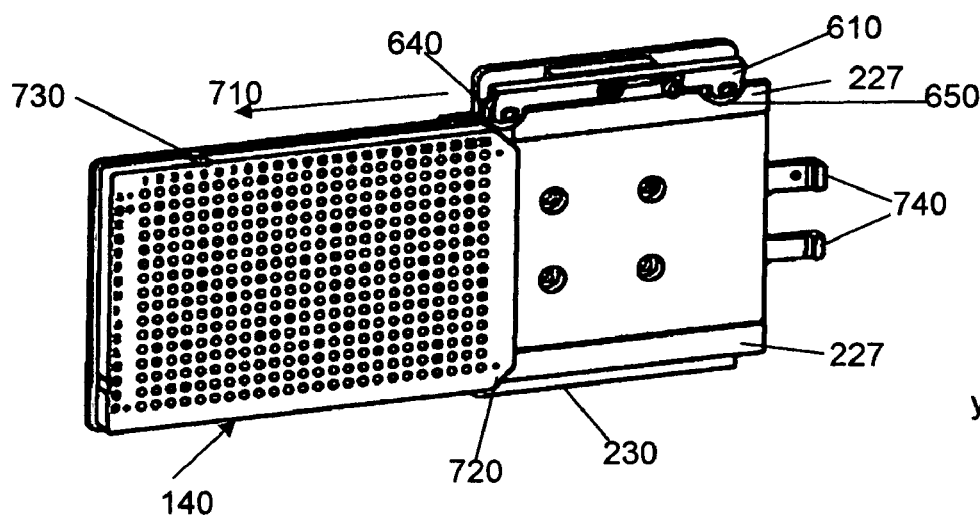
Fig. 7a
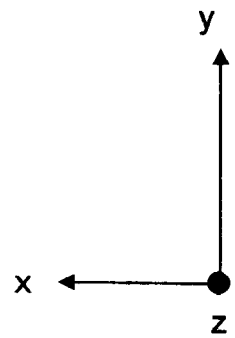

SAMPLE PLATE GRIPPING MECHANISM

FIELD OF THE INVENTION

The present invention generally relates to methods and apparatus for releasably gripping sample plates for use in mass spectrometry applications. This invention also relates to methods and apparatus for gripping mechanisms that enable transference of sample plates from one gripping mechanism to another.

BACKGROUND OF THE INVENTION

The Matrix Assisted Laser Desorption Ionization (MALDI) technique involves depositing a sample (analyte) and a matrix dissolved in a solvent as a spot on a sample plate. After the solvent has evaporated, the mixture of sample and matrix is left on the sample plate. Typically, the sample plate bearing the sample spot is inserted into an mass analyzer or into a sample source adjacent a mass analyzer. The mass analyzer is typically pumped out to provide a substantially vacuum environment before the sample at each spot is analyzed. The MALDI technique requires that a pulse from a laser irradiate the matrix and causes it to evaporate. The sample is then carried with the matrix, ionized, and eventually analyzed by the mass analyzer.

Matrix Assisted Laser Desorption/Ionization (MALDI) is often combined with time-of-flight (TOF) mass spectrometry, Fourier Transform Ion Cyclotron Resonance, quadrupole ion trap, and triple quadrupole mass spectrometers, providing for detection of large molecular masses.

MALDI sample plates are typically formed of stainless steel having a highly polished and flat surface. The plates may be adapted to fit into and to be handled by automated handling apparatus employed to transport and position the plates within the mass spectrometer instrument, and optionally to transport the plates between different stations in an automated analysis train (e.g., between automated sample deposition equipment and the mass spectrometer).

The transferring a sample plate from one gripping mechanism to another produces a localized stress point which typically results in yielding the surface material due to a constant clamping force applied during the transference. This frictional point contact made with a sample plate can cause galling of the sample plate and the member that makes contact with it. Therefore when gripping or releasing a sample plate, material removal or addition can occur. The effects of material removal or buildup due to frictional surface conditions cause locking and resistance build up between the sample plate and the member it is contacting which effects planarity alignments and accuracy of parts. Ultimately, this means that when a sample plate is transferred from one gripping means to another, the degree of repeatability and reliability can be destroyed. Typically dissimilar metals, polymers or coating surfaces are used with varying degrees of lubricity avoiding premature surface deterioration failures.

SUMMARY

This invention provides novel methods and apparatus for releasably gripping MALDI sample plates so they can be analyzed by a mass analyzer. This invention enables reliable transfer of a typical rectangular, square or lipped structured sample plate, such as a microtitre plate by using only the sample plate features or the sample plate structure given. No additional aids must be attached to the sample plate in order to transfer or handoff. This invention also provides novel methods and apparatus for facilitating the transfer of a sample plate from one environment to another within a mass spectrometer system in a reliable and repeatable manner.

An apparatus for releasably gripping a sample plate for use with a mass spectrometer has been developed, the sample plate having substantially parallel faces and a peripheral surface. The apparatus comprises a planar member having opposed lateral and end peripheral surfaces; a first guiding structure disposed along one lateral peripheral surface, and a second guiding structure disposed along the opposing lateral peripheral surface. The first and second guiding structures are positioned on the planar member to accommodate the sample plate and allow the sample plate to be releasably gripped. The second guiding structure comprises a biasing mechanism which when activiated, provides a force that forces the second guiding structure towards the peripheral surface of the sample plate such that the sample plate is retained by the apparatus.

Particular implementations can include one or more of the following features. The sample plate can include a sample plate adapter. The sample plate can be vertically orientated within the mass spectrometer. The sample plate can be held repeatably within the range of less than 40 microns.

The apparatus can securely locate the sample plate in three translational coordinate axes. The apparatus can be operated to minimize frictional contact, prevent galling thus preventing the sample plate from locking and improving repeatablility. The apparatus can comprise a stop that limits the distance the sample plate can be guided into the apparatus.

The second guiding means may comprise a rocker arm. The force that forces the second guiding structure towards the peripheral surface of the sample plate can be opposed on the same peripheral surface by the first guiding structure. The biasing mechanism may not be activated until the first and second guiding structures have traversed a substantial portion of the peripheral surface of the sample plate. The biasing mechanism can be configured to apply a force having components both in and orthogonal to the plane of the sample plate. The biasing mechanism may be caused to be stably positioned on the sample plate, by a detent in the sample plate.

Unless otherwise defined, all technical and scientific terms used herein have the meaning commonly understood by one of ordinary skill in the art to which this invention belongs. In the case of conflict, the present specification, including definitions, will control. Unless otherwise noted, the terms "include", "includes" and "including", and "comprise", "comprises" and "comprising" are used in an open-ended sense—that is, to indicate that the "included" or "comprised" subject matter is or can be a part of component of a larger aggregate or group, without excluding the presence of other parts or components of the aggregate or group.

The details of one or more implementations of the invention are set forth in the accompanying drawings and the description below. Further features, aspects, and advantages of the invention will become apparent from the description, the drawings, and the claims.

BRIEF DESCRIPTION OF THE DRAWINGS

For a better understanding of the nature and objects of the invention, reference should be made to the following detailed description, taken in conjunction with the accompanying drawings, in which:

FIG. 1 is an exploded view of a sample plate and a sample plate adapter, as used in mass spectrometry applications.

FIGS. 2a-2c are schematic views of the gripping mechanism of FIG. 2, combined with the sample plate and sample plate adapter of FIG. 1.

FIG. 5 is a more detailed view of the first guiding structure.

FIG. 6 is a more detailed view of the second guiding structure.

FIGS. 7a-7c illustrate the three stages of operation of the sample plate gripping mechanism.

Like reference numerals refer to corresponding parts throughout the several views of the drawings.

DETAILED DESCRIPTION OF EMBODIMENTS

Figure 3:
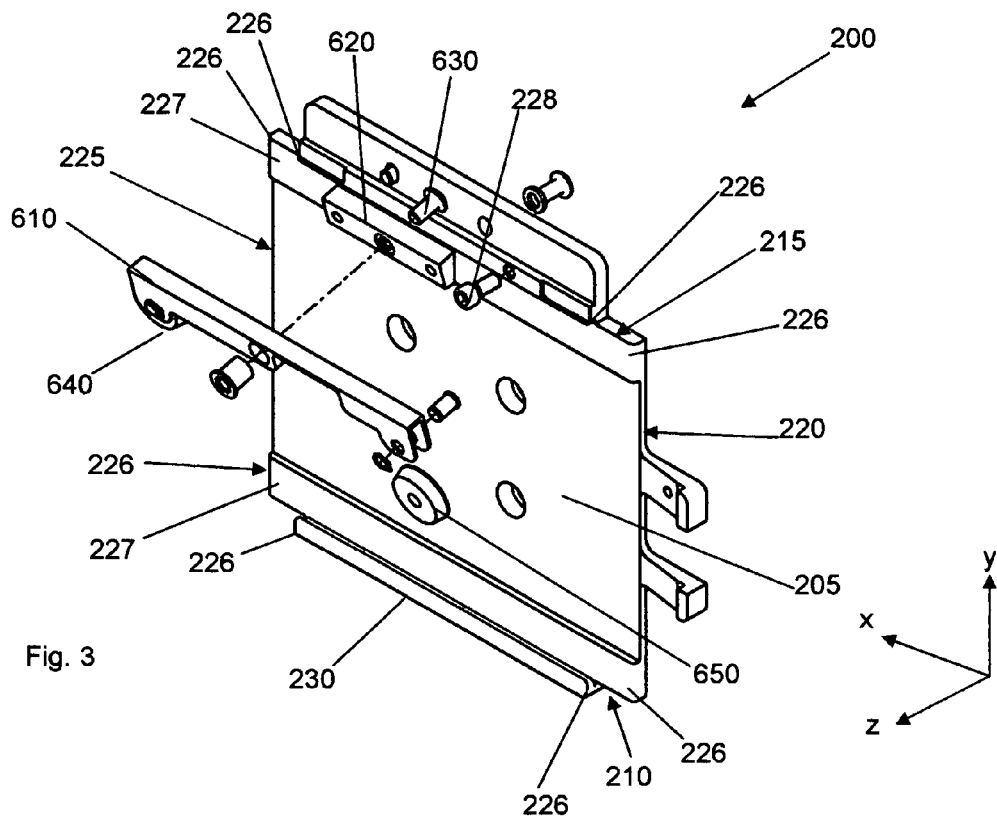
FIG. 3 is an exploded view of a sample plate gripping mechanism according to an aspect of the invention.

This invention is not limited to the particular embodiment described herein. There are a number of varied embodiments and these variations can be made by a person competent in the art and are therefore considered to be covered by the invention.

FIG. 1 illustrates a MALDI sample storage plate 100 and a sample plate adapter 150. The sample storage plate 100 is typically made of stainless steel or some other suitable material such as surgical grade stainless steel or silicon wafer, and has a top surface 110 having a plurality of target areas 120 on which sample spots are deposited, and bottom surface 130 opposite to the top surface 110. The bottom surface 130 of the sample storage plate 100 is designed to come into contact with the platform 160 of the sample plate adapter 150 to form the MALDI sample plate 190. The sample storage plate 100 has substantially parallel surfaces 110, 130 and a peripheral surface 140. The MALDI sample plate 190 is formed by releasably attaching the sample storage plate 100 to the sample plate adapter 150. The sample plate adapter 150 typically comprises metals such as aluminum or stainless steel; polymers such as PEEK, or ULTEM™; or can be coated with solid lubrication films such as molybdenum disulphide or metals such as electroless nickel. When attached, the sample plate adapter 150 forms a lip 170 where the sample plate adaptor 150 extends beyond the perimeter of the sample storage plate 100 or beyond the platform 160 of the sample plate adapter 150 (whichever is the larger). The lip 170 enables alignment of the sample plate to be attained, this feature need only be between about 0.076 inches and 0.078 inches in depth. The sample storage plate 100 and the sample plate adapter 150 are releasably coupled in a manner that inhibits the movement of the sample storage plate 100 relative to the sample plate adapter 150, the sample plate adapter 150 exerting a downward force on the sample storage plate 100 in a direction orthogonal to the plane of the sample storage plate 100.

The sample storage plate 100 may alternatively comprise another type of plate such as microtitre plates, slides, biochips, microscope slides or any other such MALDI sample plate that may store samples.

According to one aspect of the invention, a sample plate gripping mechanism 200 is an apparatus that releasably grips a sample plate 190 for use with a mass spectrometer. However FIG. 1 and the associated text depict/describe one non-limiting example of a sample plate 190 configuration that can be used in connection with the gripping mechanism 200. Other sample plates 190 can be utilized, whether they be of configured of one discrete unit or a combination of elements, and with or without a sample plate adapter associated with the sample plate. Although it is illustrated and written throughout this description that the sample plate gripping mechanism 200 is configured to grip the sample plate 190, depending upon the configuration of the apparatus, the sample plate gripping mechanism 200 may be configured to grip a sample storage plate 100, a sample plate adapter 150, or a sample plate 190.

Figure 4:
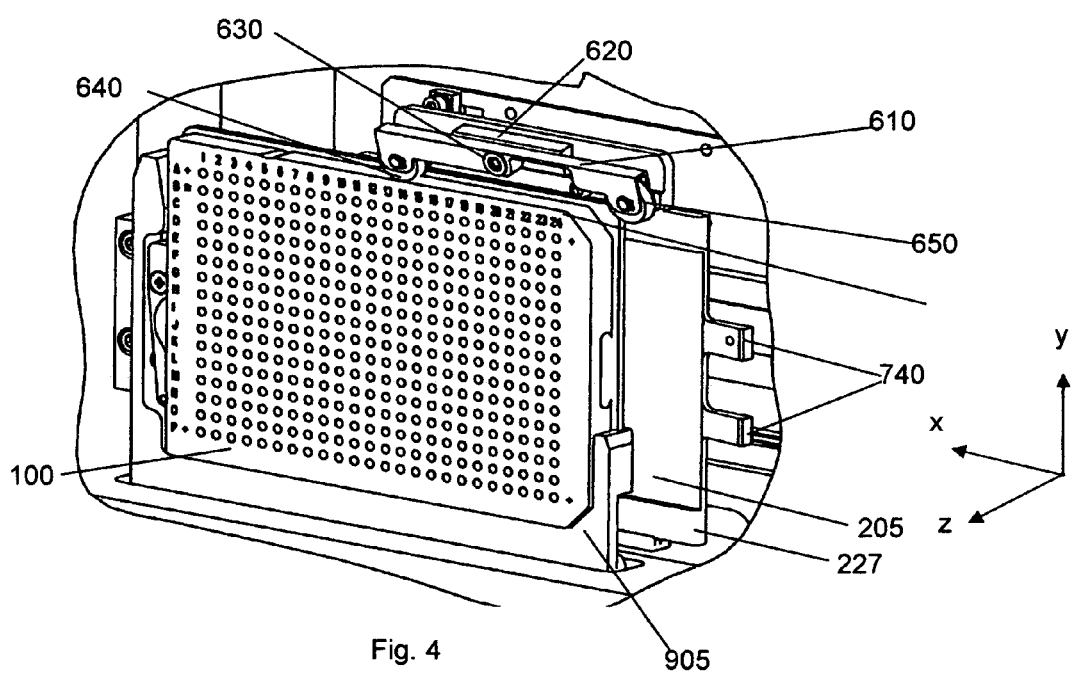
FIG. 4 is a perspective view of the gripping mechanism of FIG. 3, combined with the sample plate and sample plate adapter of FIG. 1.

The apparatus itself is constructed as follows:

FIGS. 2 and 4 illustrate the sample plate gripping mechanism 200 gripping a sample plate 190, FIG. 4 being a perspective view. FIG. 3 shows an exploded view of the sample plate gripping mechanism 200 without the sample plate 190 in place. The sample plate gripping mechanism 200 comprises a planar member 205 having opposed lateral peripheral surfaces 210, 215 and end peripheral surfaces 220, 225. A first guiding structure 230 is disposed along one lateral peripheral surface 210, and a second guiding structure 235 is disposed along the opposing lateral peripheral surface 215. The first and second guiding structures 230 and 235 respectively are spatially positioned on the planar member 205 to accommodate the dimensions of the sample plate 190 and allow the sample plate 190 to be releasably gripped. In one implementation, as illustrated, the planar member 205 also has raised areas or protrusions 227, on which the sample plate 190 rests. These protrusions 227 are substantially parallel to the plane of the planar member 205 and enable planar contact to occur between the protrusions 227 and the sample plate rather than the planar member 205 and the sample plate, thus reducing the overall contact area between these members, and thus reducing frictional forces.

In the views shown, it can be seen that the plane defined by the major axes of the sample plate 190 is substantially parallel to the plane of the planar member 205 of the sample plate gripping mechanism 200. The gripping is facilitated by the first and second guiding structures 230, 235, which are described below.

The first guiding structure 230 which is illustrated in greater detail in FIG. 5, comprises an L-shaped structure 510 along the lateral peripheral surface 210 of the planar member 205. The L-shaped structure 510 is coupled to the planar member 205 such that the combined structure forms a J-shaped structure along the lateral peripheral surface 210. The J-shaped structure defines a groove 520 which is configured to receive the complementary portion of the lip 170 formed by the sample plate 190 as illustrated in FIG. 5. The first guiding structure 230 acts as a guiding rail for guiding the lip 170 of the sample plate 190, providing guiding in the x direction. The groove 520 having a size of 0.080 to 0.082 inches in the z direction, thus enveloping the lip 170 of the sample plate 190 with a clearance.

The second guiding structure 235 comprises a biasing mechanism which is coupled to the planar member 205 and acts as a guiding rail for guiding the other lateral peripheral surface 215 of the sample plate 190, providing guidance in at least the x and z directions. The second guiding structure 235 is illustrated in more detail in FIGS. 3 and 6. In one implementation, the biasing mechanism comprises a leverage/spring element, a rocker arm 610 that is coupled via a spacer 620 and suitable coupling means 630 to provide for resilient coupling. This resilient coupling allows for the rocker arm 610 to have freedom of motion in the y and z directions under certain conditions (which will be explained later). The rocker arm 610 may comprise stainless spring steel, and may be a weighted rocker arm. A weighted rocker arm comprises two arms either side of a pivot point. The weighting is achieved from one of the arms weighing more than the other arm. In practice, this weighting effect may be achieved by utilizing material of differing mass for each arm; utilizing one arm of different structure to the other; utilizing one arm that is hollow whilst the other is solid; simply utilizing one arm of differing length to the other; or combinations of the above. The rocker arm 610 is ultimately utilized to contact the sample storage plate 100, and the pivot ratio being between 1.0 to 2.0, for example one arm having a length of substantially 1.75 inches from the pivot point 635 and the other arm having a length of substantially 1.25 inches from the pivot point 635. The second guiding structure 235 may also comprise at least two frictional elements, illustrated as rollers 640, 650, one roller disposed at each of the rocker arm 610. Each roller 640, 650 exhibits a degree of resiliency in the x, y and z directions for reasons that will be explained later. In one implementation of the invention, the resiliency is provided by configuring the rollers such that the diameter of the rollers 640, 650 is at an angle to the plane of the sample storage plate 100 as shown in FIGS. 4 and 6. In another implementation of the invention, the resiliency is provided by providing rounded edges on the frictional elements, such as providing round or shaped rollers 640, 650. The rollers 640, 650 may comprise Teflon™, PEEK, stainless steel or ULTEM™.

FIGS. 7a, 7b and 7c illustrate how the sample plate gripping mechanism 200 facilitates the sample plate to be releasable gripped. In this particular configuration, the sample storage plate 100 is vertically oriented within a sample plate handling apparatus or within a mass analyzer. However other orientations are possible. In FIG. 7a, the sample plate 190 is held by another sample plate holder (not shown, but may be similar to the sample plate holder 905 illustrated in FIG. 4). This sample plate holder may have received the sample plate manually from an operator, may be a robotic sample plate holder utilized in automated systems, or may operate by actuated magnetism or any other suitable means. The sample plate gripping mechanism 200 is disposed at one end of the sample plate 190, and moves in the x-direction as illustrated by the arrow 710.

Initially, before the first of the two rollers 640 approaches the upper peripheral surface of the sample storage plate 100, the first guiding structure 230 approaches the lower peripheral surface 140 of the sample storage plate 100. (It should be recognized that the terms "upper" and "lower" are used to denote position relative to the two respective guidance structures and are not intended to refer to different parts of the structure). As the first guiding structure 230 approached, the lip 170 of the sample plate 190 cooperates with the groove 520 in the sample plate gripping mechanism 200, and assists in guiding the sample plate adapter 150 along the groove 520, thus aligning the lower peripheral surface of the lip 170 of the sample plate adapter 150 with the first guiding structure 230, and parallel to the planar member 205 of the sample plate gripping mechanism 200. The sample plate 190 consequently attains alignment in two of the three translational axes. The leading corner of 720 of the sample storage plate 100 may be chamfered to aid alignment of the lip 170 and the groove 520.

As the motion of the sample plate gripping mechanism 200 continues in the direction of the arrow 710, the first of the two rollers 640 approaches the upper peripheral edge of the sample plate adapter 150. (It should be recognized again that the terms "upper" and "lower" are used to denote position relative to the two respective guidance structures and are not intended to refer to different parts of the structure). Again the corner of the sample plate adapter 150 may be chamfered to facilitate alignment of the first roller 640 with the sample plate adapter 150. In the event that the circumferential perimeter of the first roller 640 does not run up against the peripheral edge of the sample plate adapter 150, there are several features of the invention that enable the lip 170 of the sample plate 190 and the leading radii 226 to be engaged between the first of the two rollers 640 and the planar member 205 of the sample plate gripping mechanism 200. Firstly, the resiliency provided by the diameter of the first roller 640 being at an angle to the plane of the sample plate adapter 150. Secondly, the inherent pivotal action of the weighted rocker arm 610. Thirdly the resiliency offered by the manner in which the rocker arm 610 is coupled to the planar member 205 via the coupling means 630. The weighted rocker arm 610 allows the first roller 640 to roll in the y-direction, thus compensating for any misalignment of the sample plate 190 in that direction. The angle of the roller 640 combined with the pivot action allows the first roller 640 to move in the z-direction, thus compensating for any misalignment of the sample plate 190 in that direction also. The second guiding structure 235 thus provides a biasing mechanism both in the plane of and orthogonal to the plane of the sample storage plate 100 which aids in grasping and leading the sample storage plate 100 in whilst applying a minimal gripping force to the sample plate gripping mechanism 200. For a sample plate 190 of one pound in weight, a minimal force is defined to be less than its own weight, that is less than one pound, for example 0.5 pounds.

As the motion of the sample plate gripping mechanism 200 continues in the direction of the arrow 710, the first guiding structure 230 continues to guide the lower peripheral surface of the lip 170 of the sample plate adapter 150 and the second guiding structure 235 continues to guide the upper peripheral surface of the sample plate adapter 150 keeping the upper lip of the sample plate 190 engaged due to a screw stop 228, limiting the pivotal spring action of the rocker arm.

As motion in the direction of the arrow 710 continues, in one implementation, the rocker arm 610 comprises a flat spring with rollers 640 and 650 leveraged by a pivot point 1.25 inches on the side of the roller 640 versus 1.75 inches on the roller 650 side keeping the rocker arm 610 in the widest catch position. The rocker arm 610 is activated when the sample plate adapter 150 pushes up the second roller 650 thus deflecting the flat spring portion of the rocker arm 610. The final stoppage point is achieved when the sample plate adapter 150 contacts the stop 740. The stop 740 limits the distance that the sample plate 190 can be inserted into the sample plate gripping mechanism 200. The position is stabilized by the detent 730 on the sample plate 190. The function of the detent 730 is to stably position the biasing mechanism on the sample plate, preventing the sample plate adapter 150 from losing contact with the stop 740. This function, combined with the resiliency exerted by the rocker arm 610 locks the sample plate adapter 150 against the first guiding means 230 to its final position within the sample plate gripping mechanism 200. An additional function of the detent 730 is to increase the repeatability of the sample plate position to remain less than 40 microns each time the sample plate 190 is gripped by the sample plate gripping mechanism. The stance of the rollers 640, 650 of the rocker arm 610 is usually a distance equal or less to that of the first guiding structure 230. Eventually, the sample plate 190 is securely located in the three translational coordinate axes and precisely planarized within the sample plate gripping mechanism 200.

As the curvature in the rocker arm 610 is reduced, the rollers 640, 650 are caused to provide a force both in a downward y-direction and orthogonal towards the plane of the sample plate 190. In an aspect of the invention, the rocker arm is not activated until more than 75% of the upper peripheral surface 140 of the sample storage plate 100 has been guided into the gripping mechanism 200 by the second guiding structure 235 of the sample plate gripping mechanism 200. Typically this means that more than 75% of the lower peripheral surface 140 of the sample plate has been guided by the first guiding structure 230. Utilization of the configuration described above reduces frictional point contact thus reduces localized stress point resulting in premature failures in the guiding structures, thus in effect guarding both sample plate 190 and first guiding structure 230 from galling and/or reducing any type of material removal when gripping a sample plate 190, or releasing a sample plate 190.

Utilization of the above configuration enables alignment precision within a range of less than 40 microns to be repeatable in the x-y directions and parallel planar x-y alignment by less than 0.002 inches over a distance of 3-5 inches, in the plane of the sample plate 190.

As indicated earlier, the sample plate gripping mechanism 200 may be utilized to facilitate the transference of a sample plate from one sample plate gripping mechanism to another. This is particularly useful when transferring a sample plate from an environment of a first pressure value (such as at atmospheric pressure) to that of a second pressure value (such as at substantially a vacuum). This is achieved without the help of any electromechanical device resulting in a low outgassing, reliable exchange mechanism without substantial heat generation. Utilization of the invention prevents locking or excessive debris generation in a vacuum environment between a sliding contact between a peripheral surface of the sample plate and a sample plate gripping mechanism while maintaining excellent surface planarity.

Figure 8:
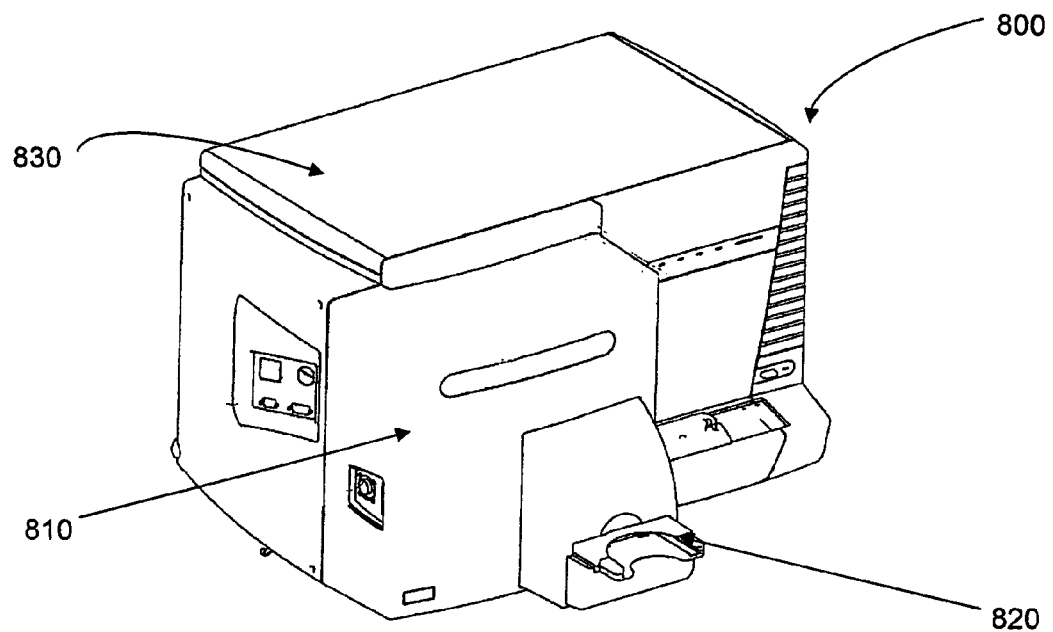
FIG. 8 illustrates a mass spectrometer combined with a sample plate handling apparatus.
Figure 9:
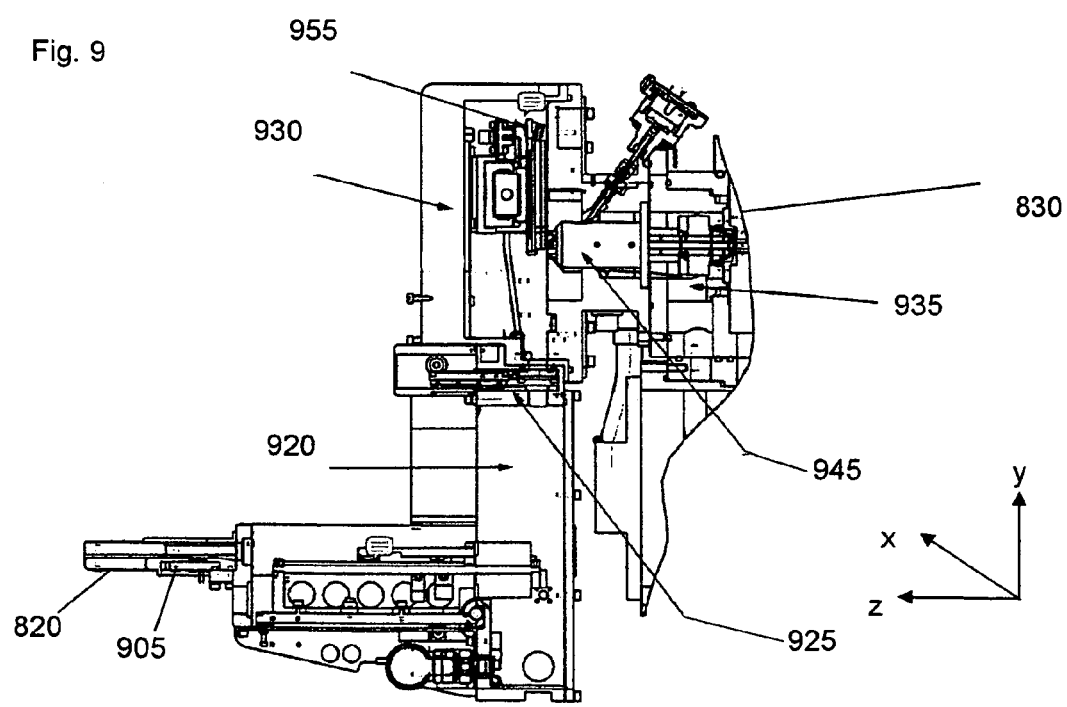
FIG. 9 illustrates a mass spectrometer combined with a sample plate handling apparatus which includes a sample plate gripping mechanism according to the current invention.

FIGS. 8 and 9 illustrate more detailed views of a sample plate handling apparatus 810 according to an aspect of the invention its associated mass analyzer 830. A sample plate receiver 820 receives the sample plate 190 (not shown) in a first plane (the x-z plane) as defined by the major axes of the sample plate 190.

In one implementation, the sample plate receiver 820 includes a transfer mechanism at one end of which is a sample plate holder 905. In a first extended form, the transfer mechanism enables the sample plate holder 905 to grip the sample plate 190 without causing unnecessary distress to the sample storage plate 100 itself or the samples thereon. The sample plate holder 905 may be any gripping mechanism known in the art, for example a magnetic means which when activated facilitates gripping of the sample plate 190 to occur. In one implementation, the sample plate holder 905 is in the form of an extended fork (as illustrated in FIG. 4). The transfer mechanism subsequently retracts the sample plate 190 into the sample plate receiver 820 such that the sample plate holder 905 and the sample plate 190 it is gripping reside primarily within the sample plate receiver 820. Electrical sensors define the extension and retraction limits of the sample plate holder 905 within the sample plate receiver 820.

A translation means translates the sample plate 190 into a second plane, typically a plane orthogonal to that of the sample plane (the x-y plane), and into the transition chamber 920 of the sample handling apparatus 810. In one aspect of the invention, the translation means is a pivot device located at the other end of the transfer mechanism.

The transition chamber 920 of the sample plate handling apparatus 810 is configured to couple via a gate 925 to a pressure chamber 930. The pressure chamber 930 is in turn coupled to a vacuum chamber 935 of the mass analyzer 830.

Once translated into the x-y plane, the transfer mechanism extends the sample plate holder 905 through the gate 925 and into the pressure chamber 930. The sample plate 190 is transferred from the sample plate holder 905 to a relocation means. The relocation means resides in the pressure chamber 930 and is responsible for positioning the sample plate 190 such that the impingement of a beam of radiation in a MALDI ion source is aligned with a select region of the sample storage plate 100, such that the major or central axis of travel of the ionized particles emanating therefrom substantially align with the ion transfer optics 945 of the mass analyzer 830. In one implementation the relocation means takes the form of a sample plate gripping mechanism 200 that is mounted onto a corresponding X-Y stage 955 as known in the art which relocates the sample plate 190 in the pressure chamber 930, in a plane that is typically substantially parallel to the x and y axes. The sample plate gripping mechanism 200 may comprise a sample plate gripping mechanism similar to that described above.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. For example, the means provided to facilitate resiliency in the second guiding structure was illustrated in the form of rollers, however alternative forms or structure could be utilized to provide the same functionality, such as blocks made of a similar material.

The embodiments were chosen and described in order to best explain the principles of the invention and its practical applications, to thereby enable others skilled in the art to best utilize the invention and various embodiments with various modifications as are suited to the particular use contemplated.

What is claimed is:

1. An apparatus for releasably gripping a sample plate for use with a mass spectrometer, the sample plate having substantially parallel faces and a peripheral surface, and the apparatus comprising:

a planar member having opposed lateral and end peripheral surfaces;

a first guiding structure disposed along one lateral peripheral surface;

a second guiding structure disposed along the opposing lateral peripheral surface;

the first and second guiding structures positioned on the planar member to accommodate the sample plate and allow the sample plate to be releasably gripped; and the second guiding structure comprising a biasing mechanism which when actuated, provides a force that forces the second guiding structure towards the peripheral surface of the sample plate such that the sample plate is retained by the apparatus.

2. The apparatus according to claim 1, wherein:
the force that forces the second guiding structure towards the peripheral surface of the sample plate is opposed on the same peripheral surface by the first guiding structure.

3. The apparatus according to claim 1, wherein:
the sample plate includes a sample storage plate and a sample plate adapter.

4. The apparatus according to claim 1, further comprising:
a stop that limits the distance the sample plate can be guided into the apparatus.

5. An apparatus according to claim 1, wherein:
the sample plate is vertically orientated within the mass spectrometer.

6. An apparatus according to claim 1, wherein:
the biasing mechanism is not actuated until the first guiding structure has traversed a substantial portion of the lip of the sample plate.

7. An apparatus according to claim 5, wherein:
the substantial portion of the lip equates to more than fifty percent of the a peripheral surface of the sample plate.

8. An apparatus according to claim 1, wherein:
the biasing mechanism is configured to apply a force having components both in and orthogonal to the plane of the sample plate.

9. An apparatus according to claim 1, wherein:
the second guiding means comprises a rocker arm, and when force is applied to the biasing mechanism, the rocker arm is caused to pivot and deflect.

10. An apparatus according to claim 7, wherein:
the rocker arm is a weighted rocker arm.

11. An apparatus according to claim 9, wherein:
the weighting of the rocker arm is such that the rocker arm remains open when the leverage ratio is 1.75 inches to 1.25 inches.

12. An apparatus according to claim 8, wherein:
the second guiding means comprises 2 rollers, a roller at each end of the rocker arm.

13. An apparatus according to claim 11, wherein:
the rollers exhibit a degree of resiliency to permit the peripheral edge of the sample plate to contact the rollers.

14. An apparatus according to claim 12, wherein:
the resiliency is provided at least partially by the diameter of the rollers being at an angle to the plane of the sample plate.

15. An apparatus according to claim 1, wherein:
the biasing mechanism is caused to be stably positioned on the sample plate by means of a detent in the peripheral surface of the sample plate.

16. An apparatus according to claim 15, further comprising:
a stop, causing the biasing mechanism to hold the sample plate repeatedly within a range less than 40 microns.

17. An apparatus according to claim 3, wherein:
the sample storage plate and the sample plate adapter are configured to form a lip, and
the first guiding structure comprises a groove, the groove accommodating the corresponding lip on a peripheral surface of the sample plate.

18. An apparatus according to claim 1, wherein:
the sample plate is securely located in three translational coordinate axes.

19. An apparatus according to claim 1, wherein:
the apparatus operates to reduce frictional contact thus preventing galling.

20. An apparatus according to claim 1, wherein:
the sample plate and the second guiding member comprises stainless steel.

* * * * *